US012626337B2

(12) United States Patent
Köster

(10) Patent No.: US 12,626,337 B2
(45) Date of Patent: May 12, 2026

(54) COMPUTER-IMPLEMENTED METHOD FOR ADJUSTING THE NOISE OF AN X-RAY IMAGE, X-RAY FACILITY, COMPUTER PROGRAM AND ELECTRONICALLY-READABLE DATA MEDIUM

(71) Applicant: Siemens Healthcare GmbH, Erlangen (DE)

(72) Inventor: Niko Köster, Neunkirchen am Brand (DE)

(73) Assignee: Siemens Healthineers AG, Forchheim (DE)

( * ) Notice: Subject to any disclaimer, the term of this patent is extended or adjusted under 35 U.S.C. 154(b) by 392 days.

(21) Appl. No.: 18/216,779

(22) Filed: Jun. 30, 2023

(65) Prior Publication Data

US 2024/0020794 A1     Jan. 18, 2024

(30) Foreign Application Priority Data

Jul. 15, 2022     (DE) ..................... 10 2022 207 239.1

(51) Int. Cl.
| | |
|---|---|
| *G06T 5/70* | (2024.01) |
| *A61B 6/00* | (2024.01) |
| *A61B 6/58* | (2024.01) |
| *G01T 7/00* | (2006.01) |
| *G06T 5/20* | (2006.01) |

(52) U.S. Cl.
CPC .............. *G06T 5/70* (2024.01); *A61B 6/5258* (2013.01); *A61B 6/585* (2013.01); *G01T 7/005* (2013.01); *G06T 5/20* (2013.01); *G06T 2207/10116* (2013.01)

(58) Field of Classification Search
CPC ............................... G06T 5/70; A61B 6/5258
See application file for complete search history.

(56) References Cited

U.S. PATENT DOCUMENTS

| | | |
|---|---|---|
| 2009/0097732 A1 | 4/2009 | Bohm et al. |
| 2011/0216986 A1 | 9/2011 | Stowasser |

(Continued)

FOREIGN PATENT DOCUMENTS

| | | |
|---|---|---|
| DE | 102007046941 A1 | 4/2009 |
| DE | 102009010873 A1 | 9/2010 |
| DE | 102010010447 A1 | 9/2011 |

*Primary Examiner* — Benjamin O Dulaney
(74) *Attorney, Agent, or Firm* — Lempia Summerfield Katz LLC

(57) ABSTRACT

A computer-implemented method for noise adjustment of an x-ray image recorded with an x-ray facility by an x-ray detector with image points is disclosed. In the method, image values are assigned, measured according to an incident x-ray dose, wherein the image values of the x-ray image include a first detector noise component arising from detector-internal noise and a second dose-dependent signal component arising from the imaging including quantum noise. A local, dose-dependent filter, adjusting the correlation between image points, evaluating a subarea of the x-ray image around an image point currently being processed, is applied to the image values of all image points of the x-ray image, which brings about a change of at least a part of the initial statistics of image values of the subareas to common target statistics of all subareas.

14 Claims, 2 Drawing Sheets

(56) References Cited

U.S. PATENT DOCUMENTS

| 2011/0268328 | A1* | 11/2011 | Bar-Aviv | ................... | G06T 5/70 |
| | | | | | 382/128 |
| 2017/0294034 | A1* | 10/2017 | Zhou | .................... | G06T 11/008 |
| 2017/0345132 | A1* | 11/2017 | Schlüter | ................ | G06T 11/003 |

* cited by examiner

| | |
|---|---|
| 1 X-ray facility | 7 Memory |
| 2 C-arm | 8 Recording unit |
| 3 X-ray emitter | 9 Calibration unit |
| 4 X-ray detector | 10 Filter core establishment unit |
| 5 Patient couch | 11 Noise adjustment unit |
| 6 Control facility | 12 Image processing unit |
| | 13 Interface |

COMPUTER-IMPLEMENTED METHOD FOR ADJUSTING THE NOISE OF AN X-RAY IMAGE, X-RAY FACILITY, COMPUTER PROGRAM AND ELECTRONICALLY-READABLE DATA MEDIUM

The present patent document claims the benefit of German Patent Application No. 10 2022 207 239.1, filed Jul. 15, 2022, which is hereby incorporated by reference in its entirety.

TECHNICAL FIELD

The disclosure relates to a computer-implemented method for noise adjustment of an x-ray image recorded with an x-ray facility by an x-ray detector with image points, to each of which image values measured according to an incident x-ray dose are assigned, wherein the image values of the x-ray image include a first detector noise component arising from detector-internal noise and a second dose-dependent signal component including quantum noise arising from the imaging. Additionally, the disclosure relates to an x-ray facility, a computer program, and an electronically readable data medium.

BACKGROUND

In x-ray imaging, not only the pure signals but also noise effects are contained in the image values of a recorded x-ray image. In this case, noise effects from different sources exist, which manifest themselves differently in the x-ray image and, depending on dominance, may lead to a different image impression, which may be undesirable both in respect of the optical display of the x-ray image but also poses additional challenges to image processing algorithms and evaluation algorithms.

An image value at an image point of an x-ray image may be broken down into two independent random variables. A first component of these random variables relates to noise arising from the x-ray detector, in particular from the detector electronics, which may be referred to as an offset. The second component of the image value is the actual x-ray signal, (i.e., the signal component), which however also includes quantum noise. The statistics of the detector noise component may be seen in good approximation as Gaussian-distributed (normal distribution), while the underlying statistics of the signal component and of its quantum noise are given by the Poisson-distributed x-ray field. These statistics are further modified by the modulation transfer function of the recording arrangement and also by additional noise sources during the conversion process in the scintillator, for example, by Swank noise and detector gain instabilities. Since the signal component is dose-dependent, it is dependent on the incident x-ray dose at the x-ray detector where which type of noise dominates.

However, it is precisely in respect of the further processing of x-ray images that knowledge about the noise level in x-ray images is extremely important. Examples in this regard include the correct setting of threshold values in noise reduction algorithms, the design of Look-Up Tables (LUTs) for image presentation, but also the creation of robust learning prerequisites for artificial intelligence algorithms.

Accordingly, it has already been proposed that x-ray images be pre-processed for noise adjustment before they are supplied to such image processing algorithms and/or evaluation algorithms, wherein a variance stabilization may be undertaken. As has already been explained, the variance of the quantum noise scales linearly with the x-ray dose, so that for pre-processing, for example, Look-Up Tables are proposed for the image values that take account of this dependence and stabilize the standard deviation of the noise. These types of approaches deliver good results for x-ray doses for which the quantum noise is markedly greater than the electronic noise. For lower doses these approaches are not efficient. Other proposed approaches for variance stabilization include the use of a generalized Anscombe transformation for example and attempt to take account of the Poisson Gaussian distribution of the underlying statistics. What are known as Gamma Look-Up Tables have also been proposed, which apply an assignment with a steep edge on the basis of empirical values.

All these pre-processing measures aim to stabilize the variance of the x-ray image over the dynamic range, but cannot, or may only approximately take account of the massive differences between the noise spectra, especially the noise color, of the detector noise component and of the quantum noise. While the detector noise component may be at least essentially white noise, the quantum noise is moreover filtered by the modulation transfer function of the recording arrangement, which acts on this as a low-frequency filter.

Known from DE 10 2007 046 941 A1 is a method for presentation of medical images by a reproduction facility of a diagnostic facility with a suppression of the noise. The method includes: a) one-time calibration of the signal-dependent noise, b) separation of the signal and noise components in the image, c) adjustment of the two components according to parameters set, and d) composition of the signals.

Known from DE 10 2009 010 873 A1 is a method for noise reduction of images, in which, during a rotational movement of a radiation source of a CT system around an examination object, acquired data assigned to the respective angle setting is used. From the data, a cross section of the examination object including a number of image points is established. Error values are determined for the data and for the image points. For the image point, an angle is established in each case that shows the strongest amount of a data error value for the respective image point error value in each case. For the image points, there is a division of the respective image point error value into a first value, belonging to the direction of the established angle, and a second value, belonging to another direction, e.g., at right angles to the angle established. The first and the second value are employed in a noise-reduction processing of the cross section.

Known from DE 10 2010 010 447 A1 is a method for adjustment of a noise behavior. X-ray detectors of the same model may differ individually from one another. These may have differences in the extent of noise in an image recorded with the aid of the respective x-ray detector. In the patent document, a variable is derived with the aid of an empty image that reflects the extent of the noise and this variable then determines the type and the extent of a filtering. Thus, an image processing is undertaken adjusted to the respective individual noise behavior of the respective x-ray detector.

The problem that results from this is that, even with a perfect variance stabilization, areas in which electronic noise (e.g., detector noise) dominates create a completely different image effect from areas in which quantum noise dominates. In particular in areas in which the x-ray dose lies in the range of values of the Noise Equivalent Dose (NED) of the x-ray detector, it is a difficult challenge to achieve an overall image impression over the entire x-ray image. The differences between the types of noise may be understood as bad image quality in dark areas. Added to this is that, precisely in steep Look-Up Tables for low input values, the high-frequency noise in darker areas dominated by detector noise may stand out as a disruptive image noise effect that, like a mixture of herbs containing salt and pepper, may contain sharply differentiated light and dark areas (salt and pepper noise).

SUMMARY AND DESCRIPTION

An underlying object of the disclosure is therefore to make possible a noise adjustment improved compared to the above, which in particular leads to a similar noise impression over the entire x-ray image.

To achieve this object, a computer-implemented method, an x-ray facility, a computer program, and an electronically-readable data medium are disclosed herein.

The scope of the present disclosure is defined solely by the appended claims and is not affected to any degree by the statements within this summary. The present embodiments may obviate one or more of the drawbacks or limitations in the related art.

In a method of the type stated at the outset, there is provision in accordance with the disclosure for a local, dose-dependent filter, adjusting the correlation between image points, evaluating a subarea of the x-ray image around a currently processed image point to be applied to the image values of all image points of the x-ray image in each case, which brings about a change in at least one part of the initial statistics of the image values of the subareas to common target statistics of all subareas.

It is thus proposed that a variance stabilization alone may no longer be carried out on the x-ray image but, in order to overcome different noise spectra, account may also be taken of the correlation between image points. In order to achieve this, a locally acting filter is proposed, which takes into account the x-ray dose at the corresponding image points, in particular described by the image value. In this case, the filter may be based on a transformation of the subarea of the x-ray image extending around the respective image point, including the point, wherein the transformation brings about a change in at least one part of the initial statistics of the image values of the subarea to a common target statistics of all subareas. To put it another way, the statistics are stabilized beyond a consideration of the variance, wherein the adjustment relates in particular at least to the second statistical moment (e.g., to the covariance), but over and above this however in particular at least one higher moment may also be considered, for example, the skew (third moment). Considered in this case are statistics of a vector of the image values in the respective subareas, which form local Regions Of Interest (ROIs). In order to stabilize the noise impression as a whole, at least partly the tensors (moments) greater than one are stabilized, wherein, as already mentioned, in many practical applications, which will be dealt with in greater detail further on, the noise adjustment described here may be reduced to the second moment, (e.g., the covariance matrix), since higher statistical moments become less and less visible to human observers.

In order to achieve the desired objective, the present disclosure proposes using a filter that describes a transformation, which transforms the initial statistics (input statistics) of an image value vector into desired target statistics (output statistics). Since the initial statistics are a function of the x-ray dose, this also applies accordingly for the transformation. Such a transformation is a linear transformation for the covariance matrix, for higher-order moments it is a tensor of the rank of the corresponding order.

In this case, use is made of the knowledge that such a transformation and thus this type of filter may be determined for an x-ray detector and its corresponding operating mode, because the dose-independent components of the corresponding initial statistics may be determined in advance, (e.g., in a calibration measurement). Thus, only the x-ray dose for the corresponding image point to be processed is employed in order to be able to apply the filter correctly. For each image point, the design of the filter is thus selected locally depending on dose and the filter is applied accordingly.

In this case, the x-ray dose for parametrization of the filter may be established for each image point as a function of the image value of at least one image point of the subarea, in particular of the image point to be filtered. This means that the x-ray dose for the choice of the suitable filter core for an image point may easily be established as the image value (gray value) of the image point (pixel) to be processed. In this case, an especially advantageous development of the disclosure makes provision for the x-ray dose for parameterization of the filter to be established from the result value of an in particular lowpass-filtered filter result of the x-ray image at the image point to be filtered. In this way, filter core fluctuations may be reduced, since local high-frequency outliers may no longer lead to sharply different forms of the filter at neighboring image points. The corresponding lowpass-filtered x-ray image (filter result) may solely be employed for establishing this x-ray dose and thus does not provide the basis for noise adjustment, which is carried out on the original x-ray image. In this case, the filter also evaluates the image values at the image points of the subareas in the original x-ray image, even if neighboring image points have also already provided filter results.

Trials have shown that correlations of the quantum noise, which are not negligible, for a pixel size of for example around 150 µm in the use of CsI scintillators may extend at most up to four image points away from the image point being considered. In other configurations, other image point extents of the correlations may also occur. If correlations are given at all for the detector noise components (which may occur as a result of discharge processes during readout in the readout direction of the detector), these are once more markedly shorter-range. Thus, the subareas may in particular extend quadratically around the central currently processed image point and/or be selected with a size of 5 times 5 to 9 times 9 image points. Smaller or larger subareas are not sensible, since smaller subareas do not adequately capture the correlation and larger subareas do not contain any further relevant correlation information.

Overall, with the method, not only a variance stabilization (if desired) is possible, but a further stabilization of the statistics, including image point-to-image point correlations, so that in particular a similar type of noise impression, (e.g., a similar noise spectrum), over the entire x-ray image is achieved. Thus, subsequent image processing algorithms and/or evaluation algorithms to be applied may reckon on a specific noise characteristic, be tailored to this, and thus deliver markedly improved image processing and evaluation results. In particular, differences in areas dominated by detector noise and areas dominated by quantum noise are minimized.

This leads in particular to human observers no longer being able to recognize a transition between quantum noise and electronic noise of the x-ray detector. "Salt and pepper"

noise is avoided or at least greatly reduced. Further image processing and evaluation algorithms of the image processing chain may be better adjusted to the image noise to be expected. In particular, the method of operation also allows a type of "noise standardization" for different x-ray detectors, which means that for different x-ray detectors the filters may actually be selected so that these still deliver the same target statistics, which may make it easier to find harmonized parameterizations of the image processing chain. These types of harmonized statistics are, as already indicated, also advantageous in respect of the training of artificial intelligence algorithms, of neural networks for example. An artificial intelligence algorithm, which has been trained on stabilized statistics, leads to greater robustness as regards changes in the input data. In particular, common artificial intelligence algorithms may be realized for different x-ray facilities, x-ray detectors, or imaging systems in general.

As already explained, the image value is composed of independent random variables, namely the detector noise component and the signal component, of which only the signal component is actually dose-dependent. Accordingly, the associated part statistics may also be considered independently. Since it is possible in particular to explicitly employ a dominance either of the detector noise but also of the quantum noise in a recording, in accordance with the disclosure a calibration measurement is also possible in order to measure the respective components and to establish the filter accordingly.

Thus, an expedient development may be provided in which, to establish the filter, dose-independent components of the initial statistics are established in a calibration measurement specifically for a layout of the x-ray detector and an operating mode of the x-ray detector during recording of the x-ray image. In this case, the operating mode of the x-ray detector may in particular describe the gain stage, the binning, and/or the frame rate, for a photon counting or energy discriminating x-ray detector thus the energy threshold, since these settings in particular exert an influence of the detector noise component. The layout of the detector may be described by reference to a specific model of the detector. Overall, the structure and the operating mode of the x-ray detector thus bring together all the factors influencing the dose-independent noise components. The x-ray detector may involve an image amplifier and/or an integrating or photon-counting flat panel detector.

In concrete terms, there may be provision, in a first calibration measurement, for at least an unexposed calibration image for establishing the initial statistics related to the detector noise component and/or in a second calibration measurement for at least one calibration image exposed with a measurement dose of more that the Noise Equivalent Dose (NED) of the x-ray detector, (e.g., at least half of the saturation dose of the x-ray detector), to be recorded and evaluated for establishing the initial statistics related to quantum noise. For example, a detector noise component for non-dominant quantum noise established in the first calibration measurement, (e.g., for less than ten times the noise equivalent dose), may be subtracted. In this case, use is made of the fact that the initial statistics for the detector noise component may be measured directly by dark, e.g., unexposed images. For the quantum noise, use may be made of the fact that, with higher doses, in particular x-ray doses, which are far higher than the NED, in particular ten times the NED, this dominates in the measured statistics and accordingly may be derived from these. With known flat-panel detectors, the NED may lie at less than 10 nGy, for example, 7-8 nGy. For CMOS detectors, even smaller values are conceivable. If use is now made of half the maximum linear dose (saturation dose) for the corresponding operating mode of the x-ray detector, a far higher value than the NED is already present, since the saturation dose may lie in the region of a few µGy. With the result of the calibration measurement, the relevant component of the initial statistics (which are to be stabilized) may be calculated for any given x-ray doses. The calibration information determined in the calibration measurement may then be employed as a basis for definition of the filter, as will be explained using the example of the covariance matrix in more detail below. If the quantum noise is not dominant, (e.g., in a measurement dose used for the second calibration measurement of less than ten times the NED), the result of the first calibration measurement may however be used to remove detector noise components, in particular by subtraction.

In a further embodiment, it is also conceivable to use a dose just below the NED for the second calibration measurement. The detector noise component known as a result of the first measurement may then likewise be subtracted in order to enable quantum noise components to be determined.

The desired target statistics to which stabilization is to take place may ultimately be defined within the framework of the present disclosure by using the given degrees of freedom in any given way such that they may be suited for the following applications, wherein different target statistics may also be employed for different subsequent image processing and/or evaluation acts. In this case, the form of the target statistics that definitively determine the homogeneous noise impression produced and the normalization of the dose dependence of the filter may be selected in a different way.

The target statistics may be selected tailored to an image processing algorithm and/or evaluation algorithm using the x-ray image as initial data. In this way, the already indicated "noise standardization" is in particular conceivable, which allows image processing and/or evaluation algorithms to be applied robustly even to x-ray images recorded with different x-ray detectors or, in the case of artificial intelligence, even to be learned. The only prerequisites may be those that are also to be imposed on the corresponding moments of the statistics, in the case of the covariance matrix, for example, that this is positive definite.

The form of the target statistics may be selected corresponding to the quantum noise or describing noise amounts uncorrelated and/or emulated to the detector noise component. While it is conceivable to convey the noise impression, for example, as white noise, it has proven to be especially advantageous, in particular with respect to the expectation of subsequent algorithms for the target statistics, to emulate the noise impression of the quantum noise and the corresponding correlations. In this case, it is not necessary to emulate the detector noise component of the x-ray detector used, but the detector component of another x-ray detector or even a detector-specific noise may be emulated.

A further degree of freedom is given by the normalization of the dose dependence. Here, in an expedient embodiment, there may be provision for the normalization of the dose dependence of the filter to be chosen so that the average value of the image values of the respective environment remains the same or that a variance stabilization is undertaken or that the variance is linear without offset in the x-ray dose.

The first case corresponds to normalized filter cores, in which there is ultimately division by a total sum, so that the average value of the respective subarea is kept constant by the transformation. Here, however, a change in the variance may occur.

The second possibility is the variance stabilization. In this way, although average values may change, at the same time with the correlation stabilization over the x-ray image additionally also the variance stabilization previously carried out frequently and desired is given. To this extent, an objective already known in the prior art is supplemented by further positive effects, namely stabilizations of the correlation.

The third case represents a type of mixing of the two normalization options first mentioned, where the target of the transformation is set to the signal component. Accordingly, the variance of the resulting target statistics may be proportional to the x-ray dose, wherein however no offset occurs during a vanishing x-ray dose, thus the detector noise component ultimately disappears. The result then has the effect of having been recorded by an x-ray detector with NED=0.

In another example, the normalization of the dose dependence may be selected so that a desired target dose dependency of the variance is produced.

The disclosure makes provision for the filter to be established from a transformation of the image values of an environment extending around the respective image point, including the point wherein, through the transformation, the covariance matrix of the initial statistics is adjusted to a target covariance matrix of the target statistics. In this case it may be sufficient to consider the covariance matrices, since higher statistical moments are less recognizable. However there may also be provision within the framework of the present disclosure, for example, for the skew tensor of the initial statistics to be adjusted to a target skew tensor of the target statistics by the transformation.

As already mentioned, like the image value itself, the initial statistics or the target statistics may be divided into a component assigned to the detector noise component and a component assigned to the signal component. Since the detector noise component and the signal component are uncorrelated, the overall variance is merely the sum of the individual variances, so that the direct result is that the covariance matrix may be written as a sum of two individual part covariance matrices. Since the covariance of the signal component is directly proportional to the x-ray dose, the dose-dependent covariance matrix of both the initial statistics and also of the target statistics may be written as the sum of a first noise matrix and the product of the x-ray dose with a second noise matrix.

In other words, for determination of the transformation, a first noise matrix of the covariance matrix for the detector noise component and a second noise matrix of the covariance matrix, which, multiplied by the x-ray dose, describes the covariance of the signal component, may be established by a calibration measurement and for the transformation to be established as a solution of an equation system for adjustment to the target covariance matrix. As has already been described above, (e.g., by an unexposed calibration image and an exposed calibration image for an x-ray dose that is far greater than the NED), the corresponding statistics and thus the first noise matrix and the second noise matrix may be measured directly in a simple manner. The calibration measurement in this case, as described, specifically for the structure of the x-ray detector and the operating mode of the x-ray detector, is repeated where necessary for each operating mode or for each detector model in order to be able to take into account different detector noise components, different binnings, different sensibilities, and/or different gains and/or different energy thresholds.

From the measurement results of such a calibration measurement the complete, dose-dependent covariance matrices of the initial statistics are established. As a transformation, the linear mapping of image values onto image values of the subarea is then found that maps the covariance matrix of the initial statistics onto the target covariance matrix. In this case, for solving the equation system produced, a Choleksy decomposition of the covariance matrices may be undertaken.

In this regard, the mathematical background, in concrete terms for the covariance matrix stabilization, is now explained in greater detail below. If a random vector X with entries $X_i$, that are scalar and for example represent image values of different image points is considered, the individual entries $X_i$ may be understood as random values. The variance is then defined as:

$$\mathrm{var}[X] = E\left[(X - \mu_X)^2\right] = E\left[XX^T\right] - \mu_X^2 \tag{1}$$

with the expected values $E[X]=\mu_X$.

The covariance matrix $K_{XX}$ is the matrix, of which the (i, j) entry is the covariance of $X_i$ and $X_j$:

$$K_{X_iX_j}=\mathrm{cov}[X_i,X_j]=E[(X_i-\mu_i)(X_j-\mu_j)]. \tag{2}$$

The diagonals of the covariance matrix contain the corresponding variances. The covariance matrix is further symmetrical.

If the image value vector $X_{in}$ of the x-ray image with the covariance matrix $K_{in}$ of the initial statistics and a linear transformation {L, b} for obtaining a transformed random vector and thus image value vector $X_{out}$ with target covariance matrix $K_{out}$, $X_{out}=LX_{in}+b$ is now considered as the input random vector, the following relationship may be derived as the correlation of the covariance matrices:

$$LK_{in}L^T=K_{out}. \tag{3}$$

Since the covariance matrices are positive definite matrices, the Cholesky decomposition may be applied, according to which the covariance matrices are able to be written as the product of a lower triangular matrix with its transpose:

$$K_{in}=AA^T \text{ and } K_{out}=BB^T \tag{4}$$

Through this the equation (3) may be reformulated to:

$$LAA^TL^T=BB^T$$

$$B^{-1}LAA^TL^T(B^T)^{-1}=I \tag{5}$$

with the identity matrix I.

This equation may be rewritten in the form $QQ^T=I$, $$B^{-1}LAA^TL^T(B^T)^{-1}=I$$

$$(B^{-1}LA)(A^TL^T(B^T)^{-1})=I \tag{6}$$

$$(B^{-1}LA)(B^{-1}LA)^T=I$$

wherein the last recalculation makes use of the fact that the inverse of a transposed matrix is the transpose of the inverse matrix.

From this it may be concluded that all L, which fulfill:

$$B^{-1}LA=Q \tag{7},$$

where Q is any given orthogonal matrix, are solutions of the equation (3).

Since this is also written as:

$$L = BQA^{-1} \tag{8}$$

with the choice of the unit matrix for Q $$L = BA^{-1} \tag{9}$$

is produced as solution for L.

For a set of N image points of a subarea a random vector Y may then be formulated as:

$$Y(O_1 + S_1, \ldots, O_N + S_N) \tag{10}$$

where $O_i$ refers to the detector noise component and $S_i$ to the respective signal component.

The image points in this case may be arranged in rows and columns, which means, for $N = n \times n$ the first n amounts belong to the first row, the second n amounts to the second row etc. Since no correlation between 0 and S is present, the complete covariance matrix $K_{YY}$ may be divided into two part covariance matrices, which solely relate to correlation within the detector noise component and the signal component:

$$K_{YY} = K_{YY}^O + K_{YY}^S \tag{11}$$

Since the covariance of the quantum noise is proportional to the x-ray dose D and its correlations are not dose-dependent, this may be written as:

$$K_{YY}(D) = K_{YY}^O + D \tilde{K}_{YY}^S \tag{12}$$

wherein $$K_{YY}^O$$

is the first noise matrix, $$\tilde{K}_{YY}^S$$

the second noise matrix.

From unexposed calibration images the first noise matrix, as already mentioned, may be derived directly, for high doses, in particular at least half of the saturation dose, the second noise matrix may be established in good approximation as:

$$\tilde{K}_{YY}^S = \frac{K_{YY}(D)}{D} \tag{13}$$

Thus, after carrying out the corresponding calibration measurements, the complete covariance matrix may be calculated in accordance with the formula (12).

Thus, for a given x-ray dose, a linear transformation $L : X_{in} \rightarrow X_{out}$ may now be established in such a way that $K_{out}$ has the desired characteristics, for example, is variance stabilized for a noise spectrum corresponding to the quantum noise. As a result of the construction, L will be a lower triangular matrix.

Advantageous application cases may also exist in which the transformation is selected so that the image resolution of the subarea changes, in particular a binning is carried out.

For this, non-quadratic matrices may be selected in the transformation. If the starting point is N×N matrices and if an N×M transformation is used, M×M matrices are obtained. This may be advantageous when there is to be a reduction of the resolution, in particular a binning, since then the application of the transformation may not only be a noise adjustment, but advantageously additionally the image resolution may be adjusted to a target resolution.

From this linear transformation, a filter core may be derived in each case for the different x-ray doses for application of the corresponding filter to a specific image point. In this case, for establishing the filter, quadrate linkage may be established from the transformation for an edge image point of the subarea is expanded around the edge point with the image values of the other image points of the subarea while assuming a symmetry to all four quadrants and is used for the image point to be filtered. In particular, the edge point thus corresponds either to the first or to the last image point of the constructed random vector and along the diagonal L to the upper left-hand or lower right-hand point. In this case, it has been recognized that the first column or the last row contains the most information as a result of the triangular structure. Since however edge points are involved, the information relates to one of the four quadrants around the edge point. Formulated differently the image point is selected, e.g., in the upper left-hand or lower right-hand edge of the subarea. All information about the linkages to the other image values of the subarea is then, as seen by the edge point, only in one quadrant. Taking into consideration the isotropy of the problem, the information from the one quadrant may be transferred to the three other quadrants. As a result of the symmetry of the system, the other quadrants may thus be derived easily, wherein the weights of the individual image points may be retained during the construction process. For this, the corresponding entries with the inverse of the number of the occurrence are weighted in the filter core, for example, once for the edge point then to be interpreted as the central pixel, halved for entries on the central cross, and quartered for the remaining entries within the quadrants.

In certain examples, other approaches to construction are also conceivable for the filter cores. With the construction just described, however, the maximum possible amount of information is transferred. Within the framework of the present disclosure, it is conceivable, depending on the corresponding x-ray dose, (e.g., defined by the respective image value), accordingly to derive and to apply the filter core for each image point to be filtered, because through the calibration measurement all necessary information is present.

In order to make a more efficient implementation of the method possible, an expedient development however makes provision for filter cores of the filter for x-ray dose values covering the dynamic range of the x-ray detector to be calculated in advance, each representing an x-ray dose interval and to be kept in a memory, in order for application of the filter of the filter core assigned to the corresponding x-ray dose interval in each case to be retrieved from the memory and used. In other words, for specific x-ray dose intervals, wherein these may always represent a central x-ray dose value, filter cores are prespecified and already kept in the memory, in order at the actual run time, (e.g., during filtering of an x-ray image), not to have to calculate these. In other words, the construction of filter cores is undertaken in advance for a suitable set of x-ray dose values, which covers the dynamic range of the x-ray detector, wherein then, as a result of the corresponding gray values, a suitable pre-calculated filter core is retrieved for image points to be filtered.

In one development, when a multilayer detector is used, (e.g., a two-layer detector), or an energy-discriminating detector delivering a number of different energy images assigned to different energy intervals, (e.g., a photon-counting detector), is provided as an x-ray detector, there may be provision for the measurement results of each layer or the energy images to be noise adjusted independently as x-ray images with corresponding layer-specific or energy interval-specific filters. Multilayer detectors, in particular dual layer detectors, include a number of different detector layers, wherein a low-energy x-ray radiation may be measured in the upper layers, while high-energy x-ray radiation penetrates the upper layers and may be measured by the lower layers. In this case, the detector layers may thus as a consequence have entirely different detector layers, so that it is advantageous not to carry out the noise adjustment jointly for an overall image formed from the measurement results of all layers, but to proceed layer-specifically for sub-images as corresponding x-ray images. In this way, a targeted noise adjustment taking account of the specific characteristics of the layers may be achieved. A similar situation is produced for energy-discriminating detectors for use in multi energy imaging, for example photon-counting detectors that, with the aid of energy thresholds, may deliver a number of energy images for different energy intervals, which are then calculated with one another in order to establish desired evaluable result images. Since the energy images also have different statistics, it is expedient to undertake a reconciliation in advance of a "mixing" of the statistics.

The method for noise adjustment may be applied within the framework of a more general method for image processing, by at least one image processing algorithm and/or evaluation algorithm being applied to the noise adjustment result after the noise adjustment. In concrete terms, there may be provision that, after the noise adjustment, a denoising algorithm and/or an edge reinforcement algorithm is applied to the noise-adjusted x-ray image. Denoising, (e.g., a noise filtering), and/or edge reinforcement algorithms deliver an outstanding image quality, in particular in a robust way, since the noise characteristics are stabilized in an improved manner and thus an expected noise impression is delivered. For example, x-ray images processed in this way may then be presented for display.

As well as the method, the disclosure also relates to an x-ray facility, having an x-ray emitter, an x-ray detector, and a control facility embodied for carrying out a method. All versions relating to the noise adjustment method may be transferred by analogy to the x-ray facility, with which the advantages already stated may thus be obtained.

The control facility, which in particular may have at least one processor and at least one memory, may include functional units for carrying out the corresponding acts of the method. For example, the control facility may include a recording unit for control of the recording operation of the x-ray facility, which may also control the recording of the x-ray image. In a noise adjustment unit, as described, the filter for noise adjustment may be applied. Also, regarding further embodiments of the method, corresponding functional units of the x-ray facility may be provided, for example, a calibration unit and/or a filter core establishment unit.

A computer program is able to be loaded directly into a memory of a control facility of an x-ray facility and has program code for carrying out all the acts of a method when the computer program is executed on the control facility of the x-ray facility. The computer program may be stored on an electronically-readable data medium, which thus includes control information, which includes at least one computer program and is embodied in such a way that, when the data medium is used in a control facility of an x-ray facility, they arrange the facility to carry out the method.

BRIEF DESCRIPTION OF THE DRAWINGS

Further advantages and details of the present disclosure emerge from the embodiments described below as well as with the aid of the drawings. In the figures.

DETAILED DESCRIPTION

Figure 1:
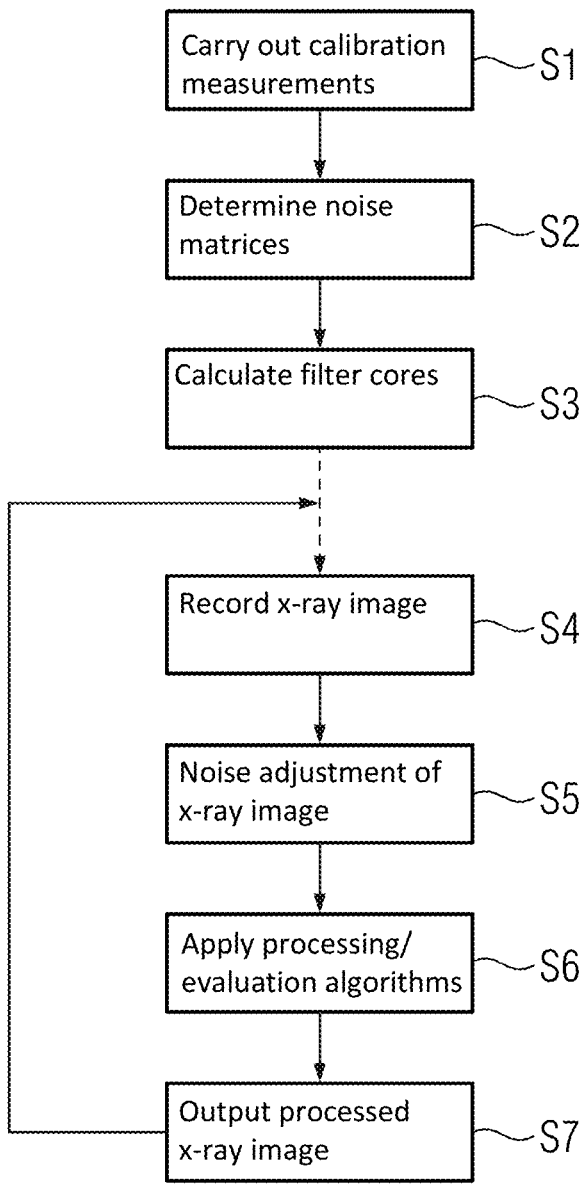
FIG. 1 depicts a flow diagram of an embodiment of the method.

FIG. 1 shows a flow diagram of an embodiment of the method. In this figure, in the present case, for a specific layout, (i.e., a specific model), of an x-ray detector and a specific mode of operation of the x-ray detector, defined by detector gain stages, binning as well as where necessary further operating parameters influencing the noise characteristics, the calibration and carrying out of a noise adjustment are described. In practice, a separate dose-dependent filter for noise adjustment is established and correspondingly applied for each operating mode and, where necessary, each layout of the x-ray detector, where necessary for each x-ray detector model.

In this case, in acts S1 to S3 to be carried out beforehand, a local, dose-dependent filter adjusting the correlation between image points, evaluating a subarea of an x-ray image around an image point currently being processed, is established. This is done in a way such that it brings about a change in at least one part of an initial set of statistics, here of the covariance matrix, of the image values of the subareas to common target statistics, here a target covariance matrix, of all subareas. In other words, a covariance stabilization takes place in that not only an adjustment is made for each image point itself, but also correlations between image points within the subareas are adjusted.

In this case, as has already been discussed, there exist degrees of freedom in respect of the choice of the target statistics, here the target covariance matrix, wherein in the present example the form of the target covariance matrix is chosen so that it reproduces the noise impression of the quantum noise. The normalization of the dose dependence of the filter is carried out so that a variance stabilization is also produced. In summary, the target covariance matrix is set constantly to the already discussed second noise matrix $$\tilde{K}_{YY}^{S},$$

so that in the filter result the variance is constant, and the noise spectrum is moreover dose independent. This choice has been made since it is also optimal for further image processing and/or evaluation algorithms to be applied after the noise adjustment in act S5.

This is of course only to be understood as being by way of example, since cases are also conceivable in which other target statistics are more suitable for following algorithms or even a number of parallel noise adjustments are carried out in order to be able to operate different following algorithms optimally.

To be able to establish the initial statistics, cf. also formula (12), in act S1, two calibration measurements are carried out. In a first calibration measurement, at least one first, unexposed calibration image is recorded, from which the detector noise component and thus the first noise matrix $$K_{YY}^0$$

may be established directly. At least one second calibration image is recorded with x-ray doses D>>NED, in particular with x-ray doses of at least half of the saturation dose (maximum linear dose). From this, it is possible to determine the second noise matrix $$\tilde{K}_{YY}^S.$$

These determinations of the first and the second noise matrix take place in act S2, the second noise matrix is then determined in particular in accordance with formula (13).

In an optional but advantageous act S3, filter cores are already prepared for different x-ray dose values covering the dynamic range of the x-ray detector, which are each representative for a corresponding x-ray dose interval, are pre-calculated and stored in a memory of the control facility of the corresponding x-ray facility, which may also carry out these method acts. For derivation of filter cores of the filters, a Cholesky-decomposition of the covariance matrix of the initial statistics (cf. formula (12)) and of the target covariance matrix in accordance with formula (4) may take place. Then, it is possible, in accordance with formula (9) to determine the linear transformation, which, applied to the image values of a subarea of the x-ray image, leads to a change of the covariance matrix to the target covariance matrix. Now, from this transformation L, the filter core of the filter to be applied for the corresponding x-ray dose value or within the corresponding x-ray dose interval to an image point, more precisely to its image value, may be constructed. The filter cores established for the corresponding representative x-ray dose values are stored, assigned to the x-ray dose intervals, in the memory of the control facility of the x-ray facility.

In cases in which no pre-computation of filter cores takes place, it is also possible to derive the corresponding transformations only during the noise adjustment itself and to construct the corresponding filter cores, wherein the procedure is as described under use of the formulas (12), (4), and (9). However, the method of operation proposed here is far more efficient with regard to time.

At a later point in time, the filter cores may then be employed accordingly for noise adjustment of recorded x-ray images. Here, in act S4, an x-ray image is recorded.

In act S5, the noise adjustment of the x-ray image then takes place, in that for each image point, depending on the x-ray dose there described by the image value, the appropriate filter core is retrieved from the memory and is applied to this image point. In this case, however, there may advantageously be provision in this context, for determination of the x-ray dose, for applying the respective image point lowpass filter to the x-ray image for establishing a filter result, wherein then the result value of the filter result is used at the image point as the x-ray dose in order to reduce filter core fluctuations.

Since the appropriate filter core, and thus the filter, has been applied to each image point of the x-ray image, the noise adjustment is concluded and both the variance and also the covariance, thus the correlation, are stabilized. This manifests itself in particular in that the noise impression of the noise adjustment result also no longer varies locally but is the same over the noise-adjusted x-ray image. In the present case, it corresponds to the noise impression (and thus noise spectrum) of the quantum noise, since constant $$\tilde{K}_{YY}^S$$

has actually been used as target covariance matrix.

In act S6, image processing algorithms and/or evaluation algorithms may then be applied to the noise-adjusted x-ray image, wherein these algorithms may be tailored in particular to the noise characteristics of the noise-adjusted x-ray image and/or vice versa, thus delivering robust outstanding results. For example, it is conceivable to obtain an image quality that is as good as possible, to apply a noise reduction algorithm, and/or an edge reinforcement algorithm to the noise-adjusted x-ray image.

In act S7, the processed x-ray image is then output, (e.g., stored), prepared for other evaluation acts, and/or displayed to a user on a display facility of the x-ray facility.

Accordingly then, as a result of the pre-calculated filter cores of the act S3, the procedure for further x-ray images, which are recorded in their turn in act S4, is highly efficient.

When a multi-layer detector is used, the noise adjustment for measurement results of the individual layers as x-ray images is carried out before these are merged to form an overall image. Accordingly, with an energy-discriminating detector, (e.g., a photon-counting detector), the noise adjustment may be undertaken for each energy image assigned to an energy interval as an x-ray image before result images are determined by combination of the energy images.

Figure 2:
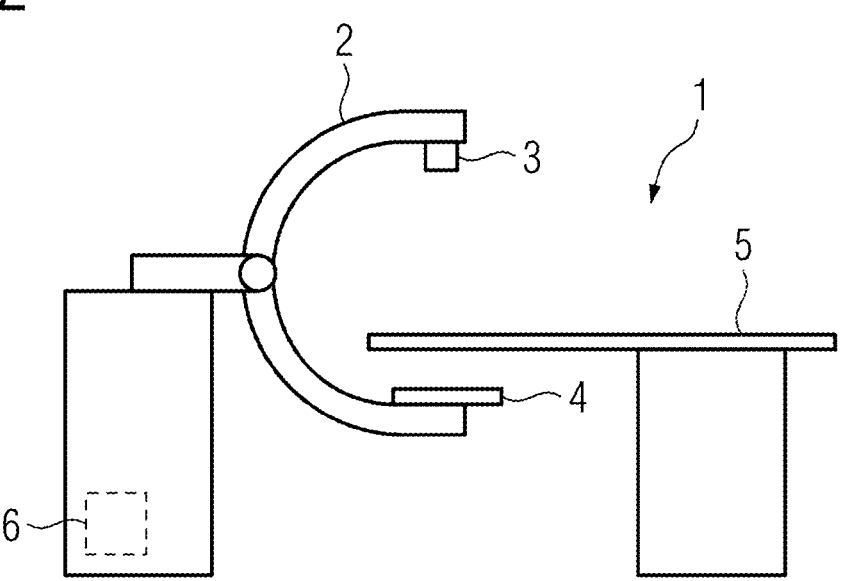
FIG. 2 depicts a basic diagram of an example of an x-ray facility.

FIG. 2 shows a basic diagram of an x-ray facility 1. In the present example, this has a C-arm 2, to which opposite one another, forming a recording arrangement, an x-ray emitter 3 and an x-ray detector 4 are arranged. By the adjustable C-arm 2, different recording geometries may be adopted with regard to a patient arranged on a patient couch 5.

The operation of the x-ray facility 1 is controlled by a control facility 6, which is embodied for carrying out the method.

Figure 3:
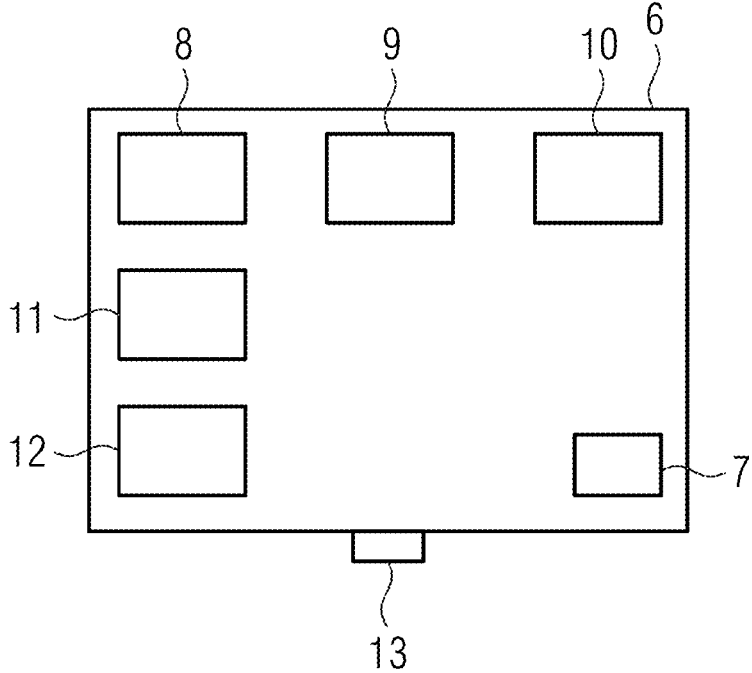
FIG. 3 depicts an example of the functional structure of a control facility of the x-ray facility.

In this regard, FIG. 3 shows the functional structure of the control facility 6 in greater detail. The control facility 6 has a memory 7, in which not only the filter cores assigned to their corresponding x-ray dose intervals are stored, but also intermediate and end results of the different processing operations.

The control facility 6 also has a recording unit 8, which controls the recording operation of the x-ray facility 1, here in particular also the recording of the calibration images in act S1 and the recording of x-ray images in act S4. In a calibration unit 9, in accordance with act S2, the first and the second noise matrix are established from the calibration images. A filter core establishment unit 10 is embodied for carrying out the pre-computation of the filter cores in accordance with act S3. These may then be stored in memory 7.

The control facility 6 further has a noise adjustment unit 11 for carrying out act S5 and an image processing unit 12 for application of image processing and/or evaluation algorithms in accordance with act S6. The processed x-ray images in accordance with act S7 may be output via an interface 13.

Although the disclosure has been illustrated and described in greater detail by the exemplary embodiments, the disclosure is not restricted by these examples and other variations may be derived herefrom by the person skilled in the art without departing from the scope of protection of the disclosure.

It is to be understood that the elements and features recited in the appended claims may be combined in different ways to produce new claims that likewise fall within the scope of the present disclosure. Thus, whereas the dependent claims appended below depend on only a single independent or dependent claim, it is to be understood that these dependent claims may, alternatively, be made to depend in the alternative from any preceding or following claim, whether independent or dependent, and that such new combinations are to be understood as forming a part of the present specification.

The invention claimed is:

1. A computer-implemented method for noise adjustment of an x-ray image recorded with an x-ray facility by an x-ray detector with image points, the method comprising:

assigning image values measured according to an incident x-ray dose, wherein the image values of the x-ray image comprise a first detector noise component arising from detector-internal noise and a second dose-dependent signal component comprising quantum noise arising from an x-ray imaging, wherein a local, dose-dependent filter adjusting a correlation between the image points, evaluating a subarea of the x-ray image around an image point currently being processed is applied to the image values of all of the image points of the x-ray image, which brings about a change of at least one part of initial statistics of image values of the subareas to a common target statistics of all subareas, wherein the local, dose-dependent filter is established from a transformation of the image values of an environment extending around a respective image point, comprising the respective image point, and wherein, by the transformation, a covariance matrix of the initial statistics is adjusted to a target covariance matrix of target statistics.

2. The method of claim 1, wherein the incident x-ray dose for parameterization of the local, dose-dependent filter is established for each image point depending on an image value of at least one image point of the subarea.

3. The method of claim 1, wherein the incident x-ray dose for parameterization of the local, dose-dependent filter is established from a result value of a lowpass-filtered filter result of the x-ray image at the respective image point to be filtered.

4. The method of claim 1, wherein, for establishing the local, dose-dependent filter, dose-independent components of the initial statistics are established in a calibration measurement specifically for a layout of the x-ray detector and an operating mode of the x-ray detector during recording of the x-ray image.

5. The method of claim 4, wherein, in a first calibration measurement, at least one unexposed calibration image for establishing the initial statistics related to the first detector noise component is recorded and evaluated, and/or wherein, in a second calibration measurement, at least one exposed calibration image with a measurement dose of more than a noise equivalent dose of the x-ray detector is recorded and evaluated.

6. The method of claim 5, wherein at least half of a saturation dose of the x-ray detector for establishing the initial statistics related to the quantum noise are recorded and evaluated.

7. The method of claim 1, wherein the target statistics are chosen: (1) tailored to an image processing algorithm and/or evaluation algorithm using the x-ray image as initial data, (2) corresponding to the quantum noise or describing noise amounts uncorrelated to the first detector noise component, (3) describing noise amounts mapped to the first detector noise component, or (4) a combination thereof, and/or wherein a normalization of a dose dependence of the local, dose-dependent filter is chosen so that an average value of the image values of the respective environment remains the same or that a variance stabilization is undertaken or that a variance is linear in the incident x-ray dose without offset.

8. The method of claim 7, wherein a skew tensor of the initial statistics is additionally adjusted to a target skew tensor of the target statistics through the transformation.

9. The method of claim 7, wherein a first noise matrix of the covariance matrix for the first detector noise component and a second noise matrix of the covariance matrix, which multiplied by the incident x-ray dose describes a covariance of the signal component, is established by a calibration measurement, and wherein the transformation is established as a solution of an equation system for the noise adjustment to the target covariance matrix.

10. The method of claim 9, wherein, for resolving the equation system, a Cholesky decomposition of covariance matrices is undertaken.

11. The method of claim 7, wherein, for establishing the local, dose-dependent filter from the transformation, a quadrant linkage established for an edge point of the subarea is expanded with the image values of other image points of the subarea while assuming a symmetry to all four quadrants around the edge point and is used for the respective image point to be filtered.

12. The method of claim 1, wherein filter cores of the local, dose-dependent filter for x-ray dose values covering a dynamic range of the x-ray detector, each filter core representing an x-ray dose interval, are pre-calculated and are stored in a memory, and wherein, for application of the local, dose-dependent filter, a filter core assigned in each case to a corresponding x-ray dose interval is retrieved from the memory and used.

13. An x-ray facility comprising:
an x-ray emitter;
an x-ray detector; and
a control facility configured to:
assign image values measured according to an incident x-ray dose,
wherein the image values of an x-ray image comprise a first detector noise component arising from detector-internal noise of the x-ray detector and a second dose-dependent signal component comprising quantum noise arising from an x-ray imaging using the x-ray emitter and the x-ray detector, wherein a local, dose-dependent filter adjusting a correlation between image points, evaluating a subarea of the x-ray image around an image point currently being processed is applied to the image values of all of the image points of the x-ray image, which brings about a change of at least one part of initial statistics of image values of the subareas to a common target statistics of all subareas, wherein the local, dose-dependent filter is established from a transformation of the image values of an environment extending around a respective image point, comprising the respective image point, and wherein, by the transformation, a covariance matrix of the initial statistics is adjusted to a target covariance matrix of target statistics.

14. A non-transitory computer readable medium comprising a computer program, which, when executed on a control facility of an x-ray facility, is configured to cause the x-ray facility to:

assign image values measured according to an incident x-ray dose, wherein the image values of an x-ray image comprise a first detector noise component arising from detector-internal noise and a second dose-dependent signal component comprising quantum noise arising from an x-ray imaging, wherein a local, dose-dependent filter adjusting a correlation between image points, evaluating a subarea of the x-ray image around an image point currently being processed is applied to the image values of all of the image points of the x-ray image, which brings about a change of at least one part of initial statistics of image values of the subareas to a common target statistics of all subareas, wherein the local, dose-dependent filter is established from a transformation of the image values of an environment extending around a respective image point, comprising the respective image point, and wherein, by the transformation, a covariance matrix of the initial statistics is adjusted to a target covariance matrix of target statistics.

* * * * *